(12) United States Patent
Sones et al.

(10) Patent No.: US 9,448,115 B2
(45) Date of Patent: *Sep. 20, 2016

(54) APPARATUS AND METHODS FOR EXTRACTING TOPOGRAPHIC INFORMATION FROM INSPECTED OBJECTS

(71) Applicant: APPLIED VISION CORPORATION, Cuyahoga Falls, OH (US)

(72) Inventors: Richard A. Sones, Cleveland Heights, OH (US); Michael L. Kress, Uniontown, OH (US); Brian M. Ensinger, Kent, OH (US)

(73) Assignee: APPLIED VISION CORPORATION, Cuyahoga Falls, OH (US)

( * ) Notice: Subject to any disclaimer, the term of this patent is extended or adjusted under 35 U.S.C. 154(b) by 120 days.

This patent is subject to a terminal disclaimer.

(21) Appl. No.: 14/450,627

(22) Filed: Aug. 4, 2014

(65) Prior Publication Data

US 2016/0033332 A1 Feb. 4, 2016

(51) Int. Cl.
*G01N 21/25* (2006.01)
*G01J 3/50* (2006.01)
*G01J 3/02* (2006.01)
*G01J 3/10* (2006.01)

(52) U.S. Cl.
CPC .............. *G01J 3/501* (2013.01); *G01J 3/0248* (2013.01); *G01J 3/10* (2013.01); *G01J 2003/106* (2013.01)

(58) Field of Classification Search
CPC ................ G01J 3/02; G01J 3/10; G01J 3/50; G01J 3/501
USPC ................................................. 356/402–425
See application file for complete search history.

(56) References Cited

U.S. PATENT DOCUMENTS

| | | | |
|---|---|---|---|
| 4,882,498 A | 11/1989 | Cochran et al. | |
| 4,972,093 A | 11/1990 | Cochran et al. | |
| 5,072,127 A | 12/1991 | Cochran et al. | |
| 5,365,084 A | 11/1994 | Cochran et al. | |
| 7,589,858 B2* | 9/2009 | Atsumi | H04N 19/85 348/266 |
| 7,684,034 B2* | 3/2010 | Sones | G01N 21/9036 356/240.1 |
| 7,812,971 B2* | 10/2010 | Jackson | G02B 7/32 356/404 |

OTHER PUBLICATIONS

Applied Vision—Cyclops Inspection System, 2014 Applied Vision Corporation.
The MVTec Insider; Surface Inspection with Photometric Stereo; MVTec, LLC, One Broadway, 14th Fl., Cambridge, MA 02141; Mar. 2014.

* cited by examiner

*Primary Examiner* — Abdullahi Nur
(74) *Attorney, Agent, or Firm* — Hahn Loeser + Parks LLP; Scott M. Oldham

(57) ABSTRACT

Systems and methods for extracting topographic information from inspected objects to identify defects in the inspected objects. A part to be inspected is illuminated with at least two different colors emitted from an illuminator providing a gradient of light consisting of the at least two different colors. A single color image of the illuminated part to be inspected is acquired, providing a color-coded topographic mapping of the part to be inspected due, at least in part, to the gradient of light. Topographic monochrome views of the part to be inspected may be generated from the single color image. Each view of the topographic monochrome views may enhance a different type of feature or defect present in the part to be inspected which can be analyzed and detected.

20 Claims, 19 Drawing Sheets

APPARATUS AND METHODS FOR EXTRACTING TOPOGRAPHIC INFORMATION FROM INSPECTED OBJECTS

TECHNICAL FIELD

Certain embodiments relate to the inspection of parts. More particularly, some embodiments relate to systems and methods to generate topographic images of parts to be inspected and to detect any defects in the parts to be inspected based on topographic information in the images.

BACKGROUND

Reliable detection of defects in shiny manufactured parts, such as the converted ends of beverage cans, has been difficult. In particular, there is a need to improve detection of scrap-in-die defects in converted-end inspection. Scrap-in-die defects are small dents caused by the accidental presence of metal fragments ("scrap") in the conversion press when a beverage shell is stamped ("converted") into a converted end. Such defects are critical, since they can cause leaks, and are often difficult to detect.

Various techniques have been tried to detect such defects. For example, acquiring multiple images of a part to be inspected under different illumination geometries to deduce three-dimensional structure has been tried. However, the particular techniques tried up to this point have not been very impressive.

Further limitations and disadvantages of conventional, traditional, and proposed approaches will become apparent to one of skill in the art, through comparison of such systems and methods with the present invention as set forth in the remainder of the present application with reference to the drawings.

BRIEF SUMMARY

In some embodiments, systems and methods for extracting topographic information from inspected objects to identify defects are provided. One embodiment includes an illuminator for machine vision applications, particularly suited for the inspection of round highly-reflective (specular) objects such as food and beverage containers (e.g., metal cans, glass bottles, plastic bottles) and related items (e.g., can ends, bottle closures). The embodiment includes a thin funnel-shaped translucent plastic diffuser illuminated from the outside with red, green, and blue (and, optionally, white) light-emitting diodes (LEDs). The top of the funnel is open, and a color camera looks down through the opening along the axis of the funnel. The object (e.g., can, bottle, closure) being inspected typically rides on a conveyor belt just below the bottom of the funnel. Red LEDs are distributed around the top of the funnel, blue LEDs are distributed around the bottom of the funnel, and green LEDs are distributed in between. The color regions may or may not overlap. The distribution of the LEDs provides a gradient of light along the direction of the axis of the funnel, which is also the optical axis defined by the orientation of the color camera and associated lens. The gradient of light imparts a color-coded topographic mapping on the inspected object which can be imaged by the color camera.

One embodiment provides a system. The system includes an illuminator, for illuminating a part to be inspected, configured to provide a gradient of light consisting of at least two different colors. The system also includes a color camera positioned near a distal end of the illuminator, defining an optical axis through an interior portion of the illuminator, wherein the gradient of light is along the direction of the optical axis. The system further includes a controller component operatively connected to the illuminator and the color camera and configured to trigger the illuminator and the color camera to acquire a single color image of the part to be inspected located near a proximal end of the illuminator. The system also includes a processing component operatively connected to the color camera and configured to receive and process the single color image to generate two or more topographic monochrome views of the part to be inspected from the single color image. The illuminator may be configured to illuminate the part to be inspected such that the acquired single color image provides a color-coded topographic mapping of the part to be inspected. The two or more topographic monochrome views may be inherently spatially registered with each other. The illuminator may include a plurality of light-emitting diodes (LEDs), providing the at least two different colors, that are segregated into channels where each channel is independently controllable by the controller component. The system may also include a power supply component configured to supply power to the illuminator, the color camera, the processing component, and the controller component. The controller component and the processing component may be configured to provide a defined combination of illumination of the part to be inspected and a color-to-monochrome transformation of the acquired single color image of the part to be inspected to allow generation of a topographic monochrome view of the part to be inspected that enhances a defined type of defect present in the part to be inspected. The gradient of light may progress substantially from a red color to a green color, and from the green color to a blue color.

One embodiment provides an illuminator. The illuminator includes a power distribution circuit board and a plurality of power delivery circuit boards each interfacing with the power distribution circuit board. The illuminator also includes a plurality of light-emitting diode circuit boards each interfacing with a corresponding power delivery circuit board of the plurality of power delivery circuit boards. Each light-emitting diode circuit board of the plurality of light-emitting diode circuit boards includes a plurality of light-emitting diodes of at least two differing colors distributed thereon to provide a color gradient of light progressing from a proximal end of the light-emitting diode circuit board to a distal end of the light-emitting diode circuit board. The power distribution circuit board may be substantially circular in shape, each of the plurality of power delivery circuit boards may be substantially triangular in shape, and each of the plurality of light-emitting diode circuit boards may be substantially trapezoidal in shape. Each of the power delivery circuit boards may interface with the power distribution circuit board at substantially a right angle, and each of the plurality of light-emitting diode circuit boards may interface with a corresponding power delivery circuit board of the plurality of power delivery circuit boards at substantially a right angle. The illuminator may further include a diffuser component configured to reside substantially within an interior portion of the illuminator to diffuse light emitted by the plurality of light-emitting diodes therethrough. The diffuser component may be substantially conical in shape and may include a flared lip portion along a proximal end of the substantially conical shape. The color gradient of light may progress substantially from a blue color to a green color, and from the green color to a red color. Each of the at least two differing colors of light-emitting diodes may be distributed substantially circumferentially and symmetrically around the illuminator. The plurality of light-emitting diode circuit boards may be arranged to form a substantially conical configuration. The illuminator may include a beam splitter component proximate a distal end of the illuminator providing on-axis illumination along a defined optical axis of the illuminator.

One embodiment provides a method. The method includes illuminating a part to be inspected with at least two different colors emitted from an illuminator providing a gradient of light consisting of the at least two different colors. The gradient of light is along a direction of an optical axis through the illuminator defined by a color camera and associated lens positioned proximate a distal end of the illuminator. The part to be inspected is positioned proximate a proximal end of the illuminator. The method also includes acquiring a single color image of the illuminated part to be inspected with the color camera and associated lens. The single color image provides a color-coded topographic mapping of the part to be inspected due, at least in part, to the gradient of light. The method further includes generating two or more topographic monochrome views of the part to be inspected from the single color image. Each view of the two or more topographic monochrome views may enhance a different type of feature or defect present in the part to be inspected. The method may further include detecting at least one defect of the part to be inspected that is present in at least one of the two or more topographic monochrome views.

These and other advantages and novel features of the present invention, as well as details of illustrated embodiments thereof, will be more fully understood from the following description and drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1:
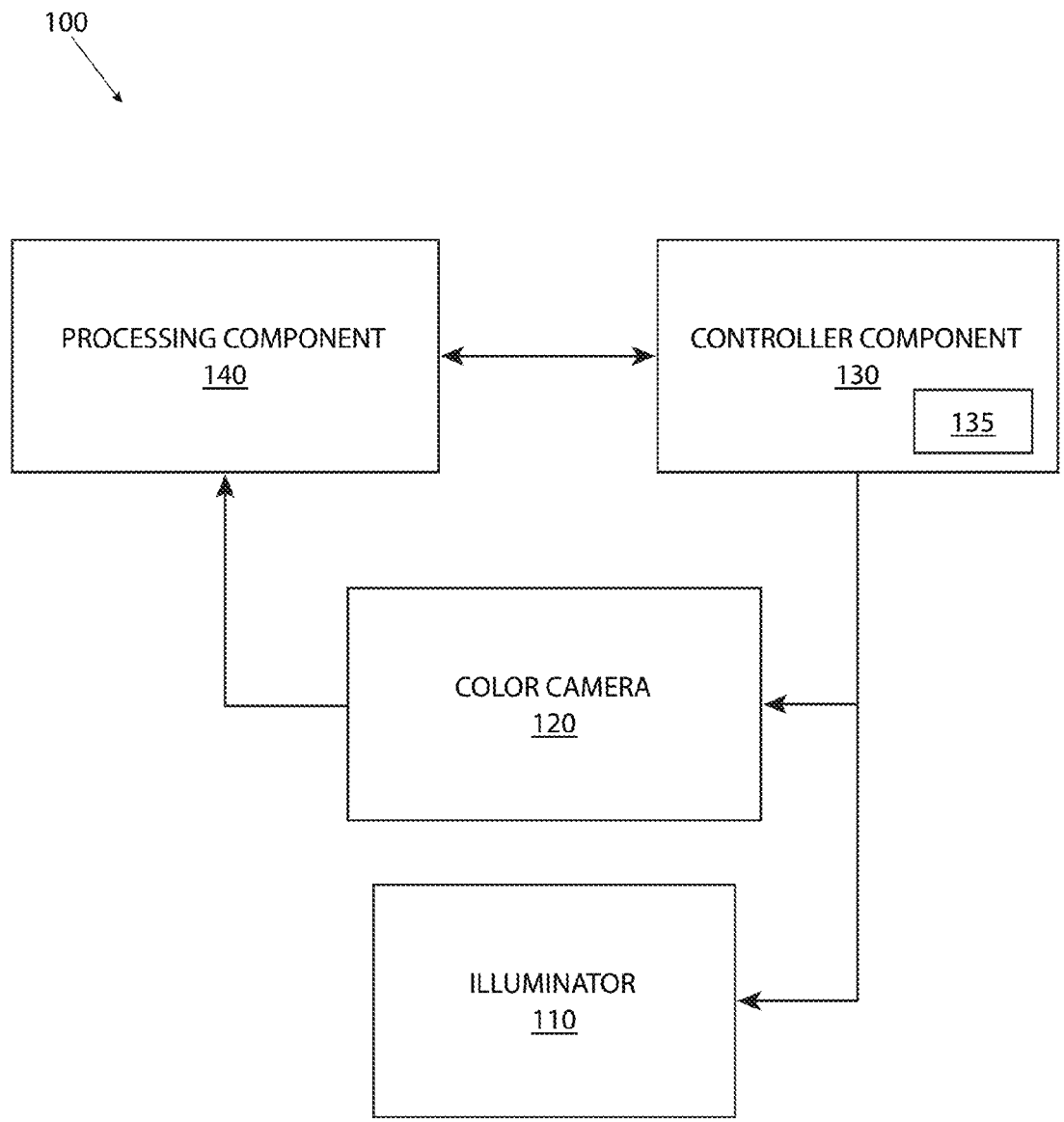
FIG. 1 illustrates an example embodiment of an imaging system to detect defects in parts to be inspected.

Embodiments of the systems and methods described herein provide for the detection and/or identification of defects and other container (e.g., beverage can) inconsistencies. In at least one embodiment, a part to be inspected (e.g., a converted end of a beverage can) is illuminated using gradient lighting and a single color image of the part to be inspected is captured. The single color image provides a color-coded topographic mapping of the part to be inspected due, at least in part, to the gradient lighting. The single color image is transformed to one or more topographic monochrome views which are analyzed to determine if the part to be inspected has any defects.

The term "substantially" as used herein means predominantly but not necessarily entirely. For example, a power distribution board may be substantially circular in shape, meaning that the power distribution board can be perfectly circular in shape, can be somewhat elliptical or oval in shape (but still largely circular), or can have some feature that causes the board to deviate from the circular shape at some portion (e.g., there may be a notch cut out of a portion of the circular board).

The phrase "the gradient of light is along the direction of the optical axis" as used herein means that the change in color of light occurs along a particular spatial direction (e.g., an up/down or z-axis direction) which is best defined by the direction of the optical axis, not necessarily that the color LEDs themselves are on the optical axis or are even arranged parallel to the optical axis. In accordance with an embodiment, the LEDs are arranged on an interior surface of a cone, formed by the plurality of light-emitting diode circuit boards, such that any contiguous line of LEDs on the interior surface of the cone running from the proximal end of the cone to the distal end of the cone is at an angle to the optical axis. However, the gradient of light (change in color of light) provided by the LEDs is still considered to be along the direction of the optical axis. In general, the color gradient runs from the bottom of the illuminator to the top of the illuminator. The phrase "single color image" as used herein means one image that has one or more colors. The phrase does not restrict the one image to having only one color.

In specific embodiments, beverage can parts to be inspected are illuminated and imaged as they move through a production line. Imaging is performed with a video camera while illumination occurs using a multi-color light source providing gradient illumination. The video camera is a color video camera having a lens. The light source (illuminator) can be strobed as parts move through the process. The illuminator includes a plurality of light emitting diodes (LEDs) emitting visible light of two or more colors. Characteristics or settings of both the camera and the LEDs can be selected or tailored to maximize differentiation between surface characteristics of the parts to be inspected in captured images.

The captured images are transmitted to various logic or processing components which perform analysis on the images. For example, edge-finding algorithms may be employed to identify certain features of a part to be inspected. Other algorithms may be employed to identify other features of the part to be inspected. Such other algorithms may include, for example, blob-finding, symmetry analysis, pixel counting, segmentation, brightness analysis, color analysis, or template matching.

While the drawings show particular components as distinct from one another, it is appreciated that components can be combined, or additional components defined, without departing from the scope or spirit of the innovation. For example, an imaging component and logic component can be combined into a single component, or combined apparatus, under the disclosures herein. The term "component" as used herein may refer to a hardware component, a firmware component, a software component, or some combination thereof. For example, the term "defect detection component" may refer to software instructions stored in computer memory that are executable on a hardware processor.

"Software" or "computer program" as used herein includes, but is not limited to, one or more computer readable and/or executable instructions that cause a computer or other electronic device to perform functions, actions, and/or behave in a desired manner. The instructions may be embodied in various forms such as routines, algorithms, modules or programs including separate applications or code from dynamically linked libraries. Software may also be implemented in various forms such as a stand-alone program, a function call, a servlet, an applet, an application, instructions stored in a memory, part of an operating system or other type of executable instructions. It will be appreciated by one of ordinary skill in the art that the form of software is dependent on, for example, requirements of a desired application, the environment it runs on, and/or the desires of a designer/programmer or the like.

"Computer" or "processing device" or "computing device" or "processor" or "processing component" as used herein includes, but is not limited to, any programmed or programmable device that can store, retrieve, and process data. "Non-transitory computer-readable media" include, but are not limited to, a CD-ROM, a removable flash memory card, a hard disk drive, a magnetic tape, and a floppy disk. "Computer memory", as used herein, refers to a storage device configured to store digital data or information which can be retrieved by a computer or processing element. The terms "controller" or "control system" or "control device" or "controller component" are used broadly herein and may be anything from a simple switching device, to one or more processors running computer-executable software instructions, to complex programmable and/or non-programmable logic circuitry. The terms "signal", "data", and "information" may be used interchangeably herein and may be in digital or analog form. The term "functionality" as used herein may refer to the logical actions and/or the supporting display screens of a system implemented in software and/or hardware.

FIG. 1 illustrates an example embodiment of an imaging system 100 to detect defects in parts to be inspected. The imaging system 100 includes an illuminator 110, a color camera 120, a controller component 130 operatively connected to the illuminator 110 and the color camera 120, and a processing component 140 operatively connected to the controller component 130 and the color camera 120. The controller component 130 controls the triggering of the color camera 120 and the illuminator 110 during image acquisition.

In accordance with an embodiment, the controller component 130 also provides for adjustment of parameter settings of the color camera 120 and the illuminator 110. For example, the controller component 130 may be configured to adjust an intensity of illumination for different LED channels of the illuminator 110. Furthermore, the controller component 130 may be configured to adjust a shutter speed of the color camera 120. In accordance with an embodiment, the processing component 140 commands the controller component 130 to make the adjustments.

The illuminator 110 illuminates parts to be inspected with a gradient of color light as the parts to be inspected are presented, one at a time, to the imaging system 100. The color camera 120 acquires a single color image of each part to be inspected. The color images acquired by the color camera 120 are communicated to the processing component 140 where the color images are processed to determine if there are any defects in the corresponding parts to be inspected.

Figure 2:
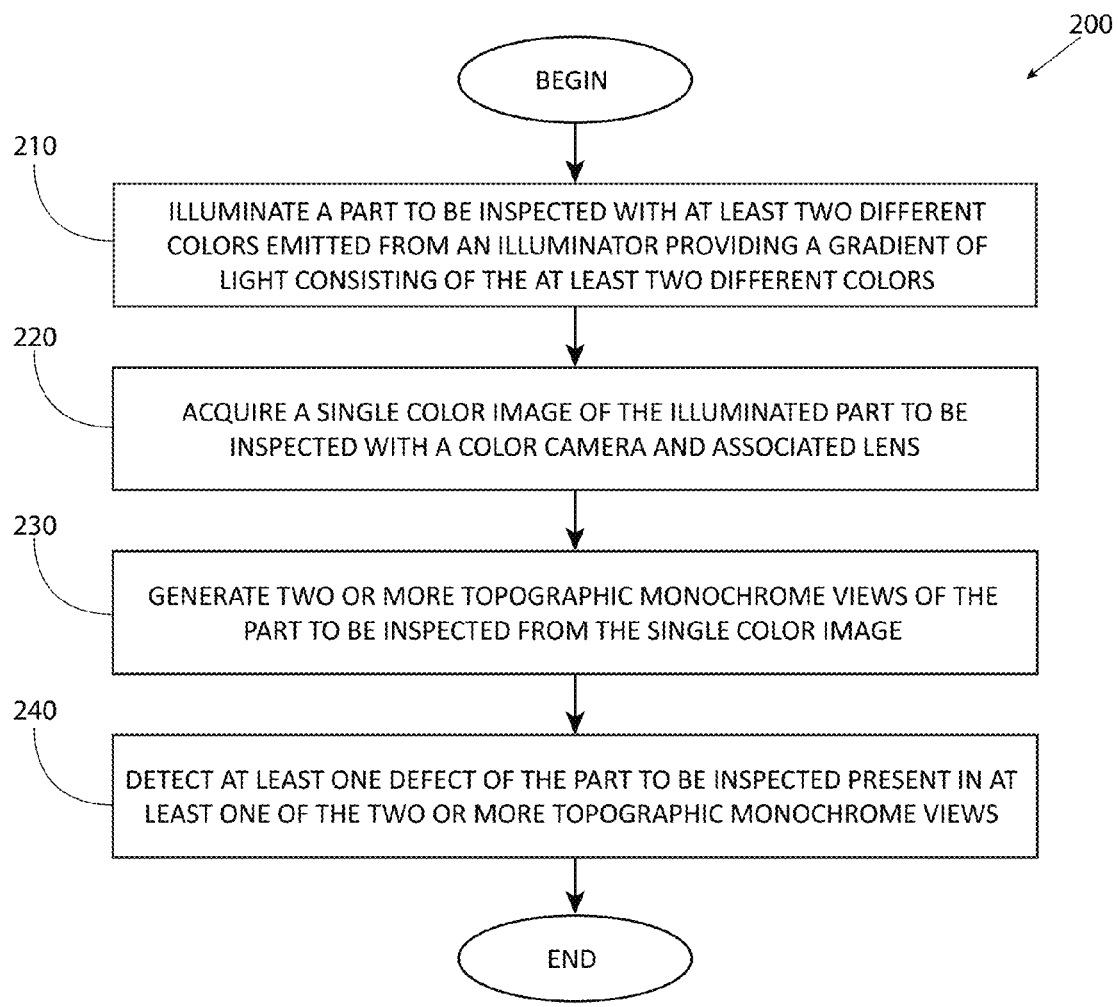
FIG. 2 is a flow chart of an example embodiment of a method for detecting defects in parts to be inspected using the imaging system of FIG. 1.

FIG. 2 is a flow chart of an example embodiment of a method 200 for detecting defects in parts to be inspected using the imaging system 100 of FIG. 1. In step 210, a part to be inspected is illuminated with at least two different colors emitted from an illuminator, providing a gradient of light consisting of the at least two different colors. In step 220, a single color image of the illuminated part to be inspected is acquired with a color camera and associated lens. In step 230, two or more topographic monochrome views of the part to be inspected are generated from the single color image. In step 240, at least one defect of the part to be inspected present in at least one of the two or more topographic monochrome views is detected. Defects may be detected by processing at least one of the two or more topographic monochrome views using image processing tools (e.g., algorithms) that operate on the image data (e.g., digital image data) of the monochrome views. The conversion to monochrome views allows certain characteristics to be emphasized while de-emphasizing certain other characteristics.

Figure 3:
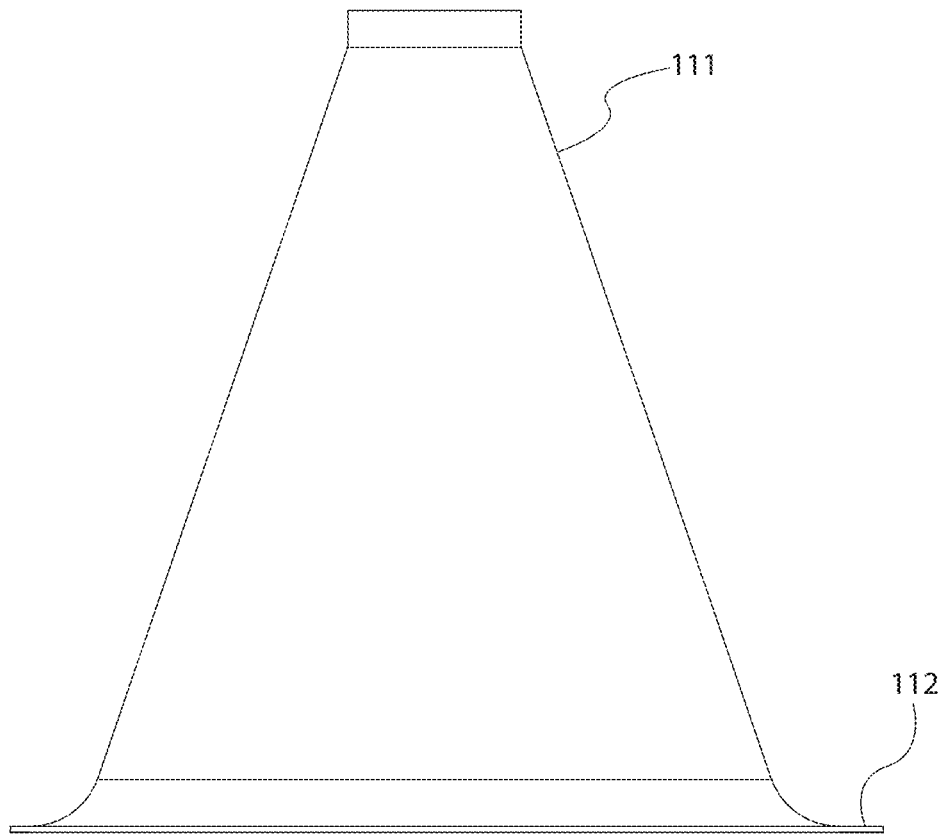
FIG. 3 illustrates a side view of an example embodiment of a diffuser component of an illuminator of the imaging system of FIG. 1.

FIG. 3 illustrates a side view of an example embodiment of a diffuser component 111 of the illuminator 110. The diffuser component 111 is configured to reside substantially within an interior portion of the illuminator 110 to diffuse light emitted by a plurality of light-emitting diodes therethrough. The diffuser component 111 is substantially conical in shape (e.g., a funnel shape) and includes a flared lip portion 112 along a proximal end of the conical shape. The flared lip portion 112 serves to illuminate further around bended corners of the inspected part. In accordance with an embodiment, the diffuser component 111 is made of a translucent plastic material such as, for example, a naturally bright and high impact polystyrene material.

Figure 4:
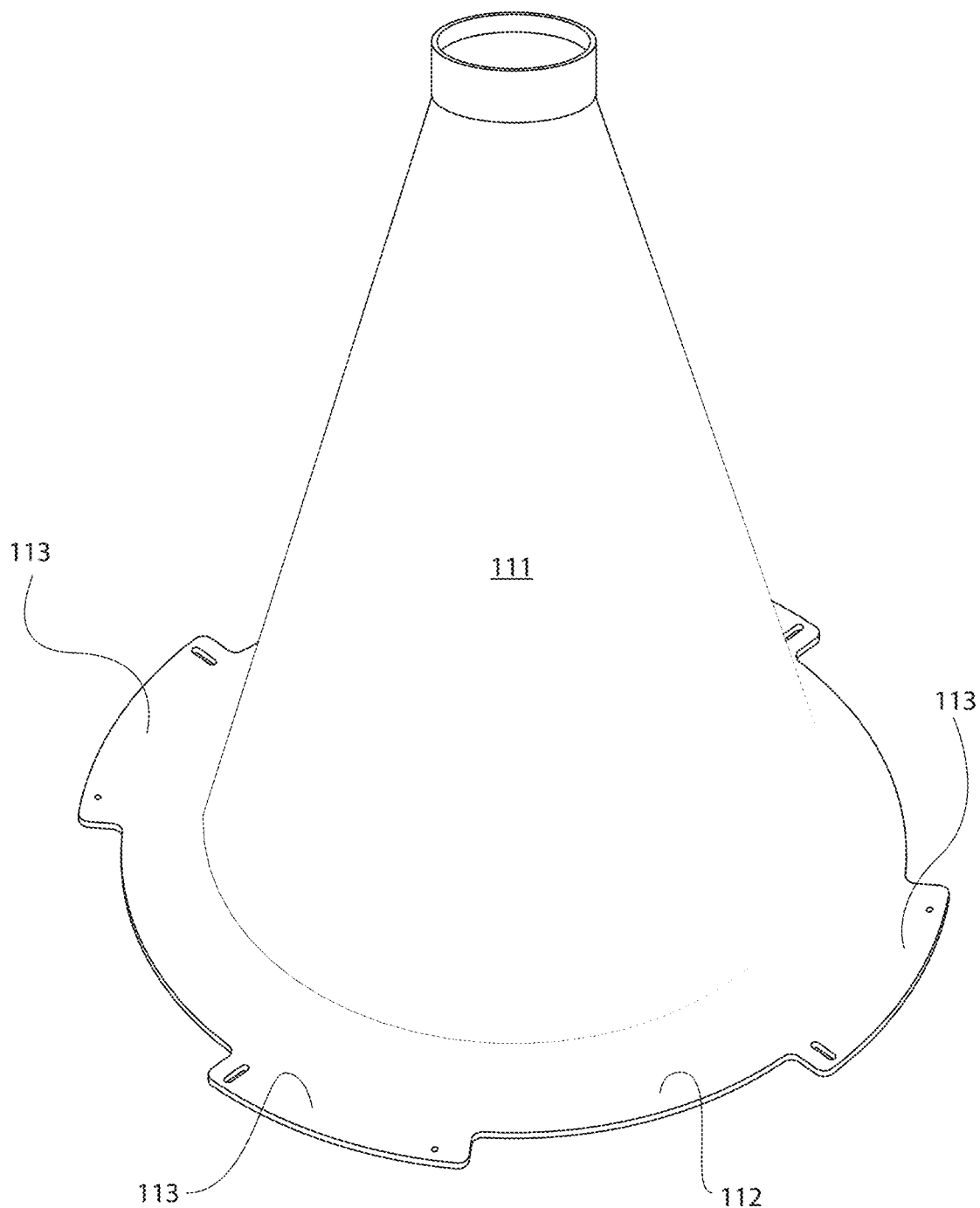
FIG. 4 is a perspective view of the diffuser component of FIG. 3 showing a lip portion and connecting portions.
Figure 5:
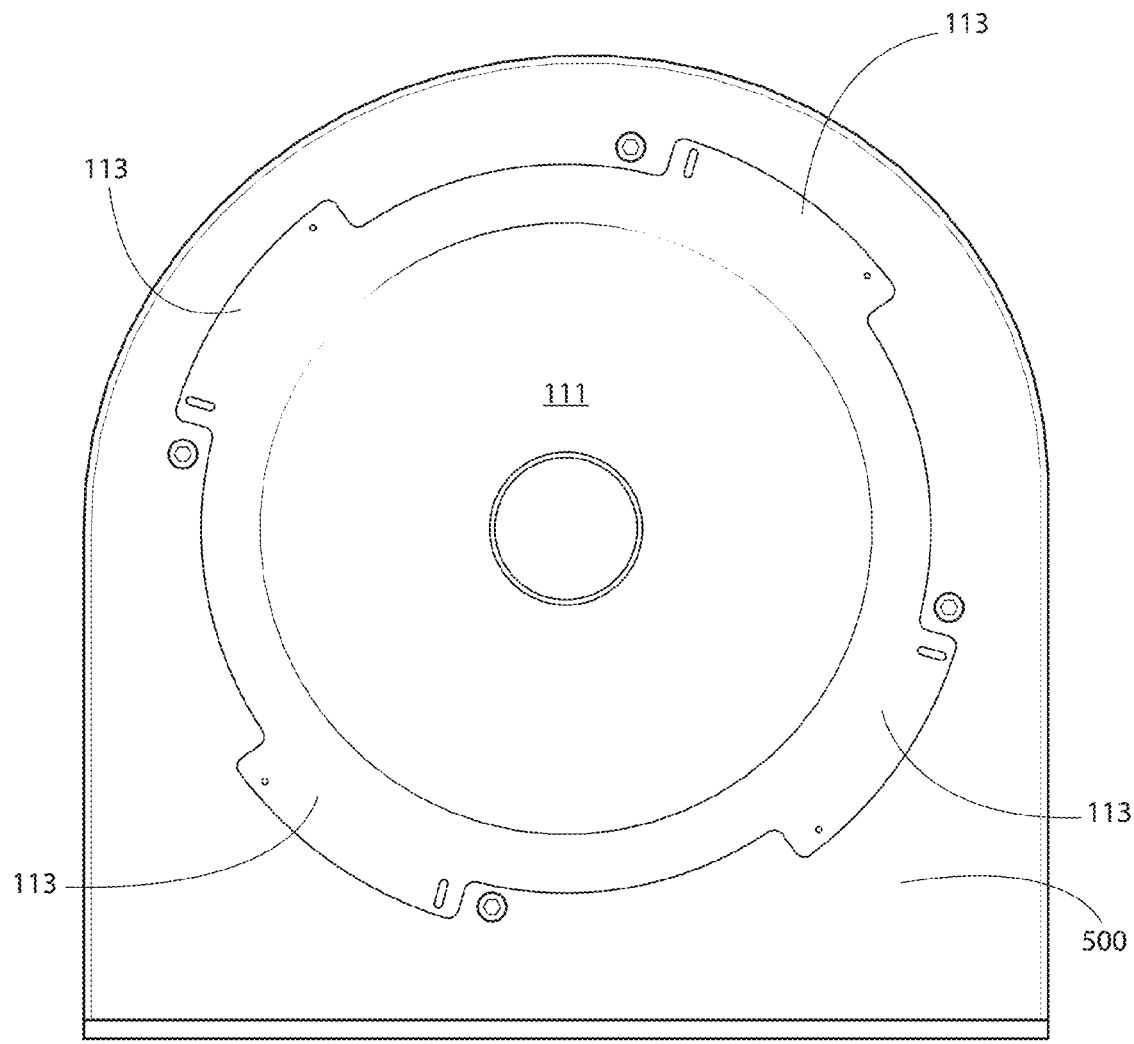
FIG. 5 illustrates an example embodiment of the diffuser component of FIG. 3 connected to a frame component of the illuminator via connector portions.
Figure 6A:
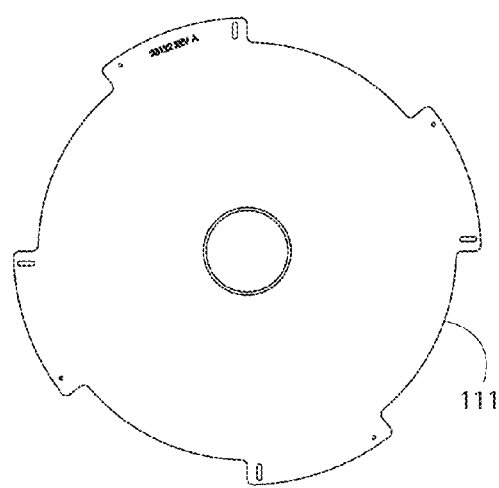
FIG. 6 shows several dimensioned views of an embodiment of the diffuser component of FIG. 3.
Figure 6B:
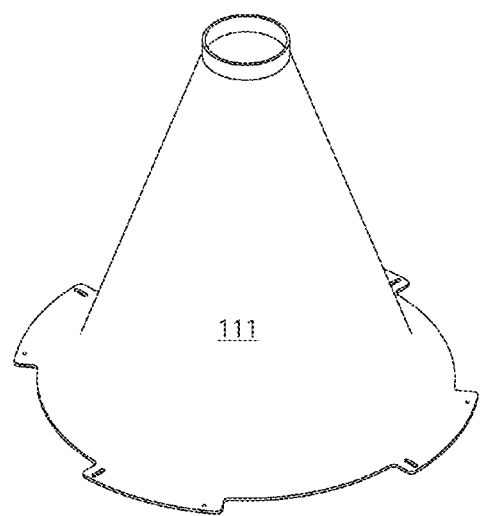
Figure 6C:
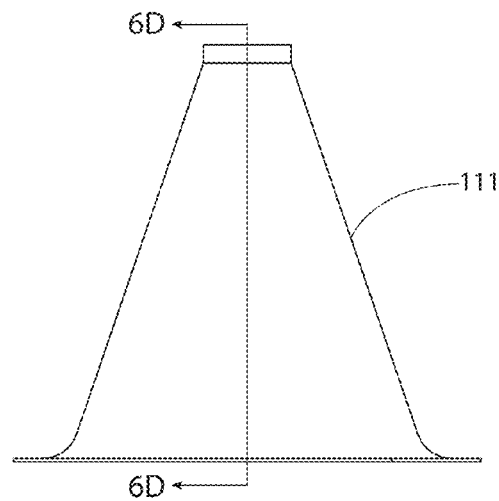
Figure 6D:
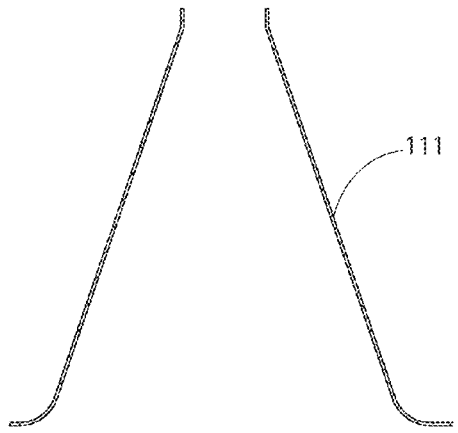

FIG. 4 is a perspective view of the diffuser component 111 showing the lip portion 112 and connecting portions 113. FIG. 5 illustrates an example embodiment of the diffuser component 111 connected to a frame component 500 via the connecting portions 113. In accordance with an embodiment, the diffuser component 111 may be twisted with respect to the frame component 500 and snap into position on the frame component 500. Similarly, the diffuser component 111 may be untwisted and unsnapped from the frame component 500. FIG. 6 shows several dimensioned views of an embodiment of the diffuser component 111.

Figure 7:
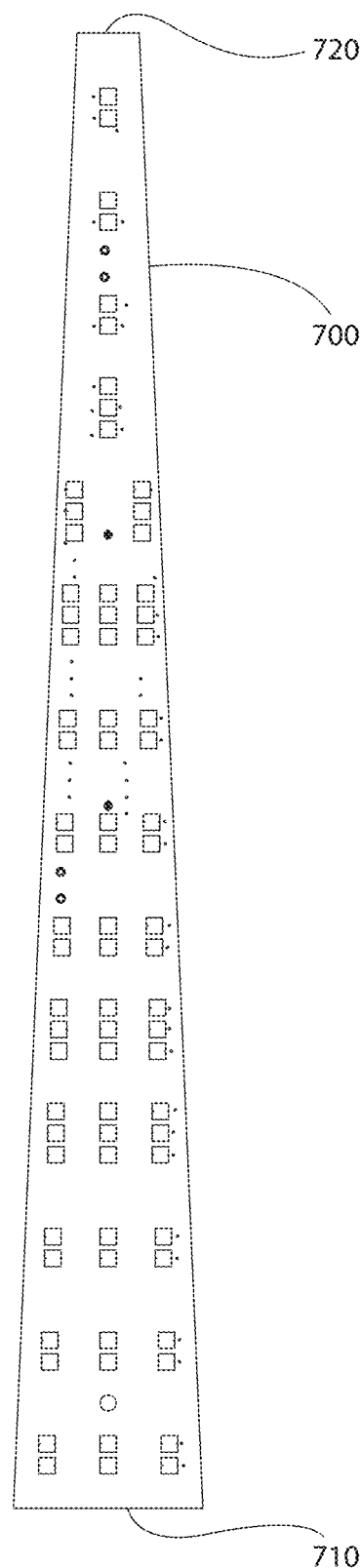
FIG. 7 illustrates an example embodiment of a light-emitting diode (LED) circuit board of the illuminator of the imaging system.

FIG. 7 illustrates an example embodiment of a light-emitting diode (LED) circuit board 700 of the illuminator 110. The LED circuit board 700 is trapezoidal in shape and includes a plurality of LEDs of three different colors (red, green, and blue) that may be surface mounted thereon. The plurality of LEDs are distributed to provide a color gradient of light progressing from a proximal end 710 of the LED circuit board 700 to a distal end 720 of the LED circuit board 700. In accordance with an embodiment, the gradient of light progresses from a blue color to a green color, and from the green color to a red color, from the proximal end 710 to the distal end 720 of the LED circuit board 700.

Figure 8:
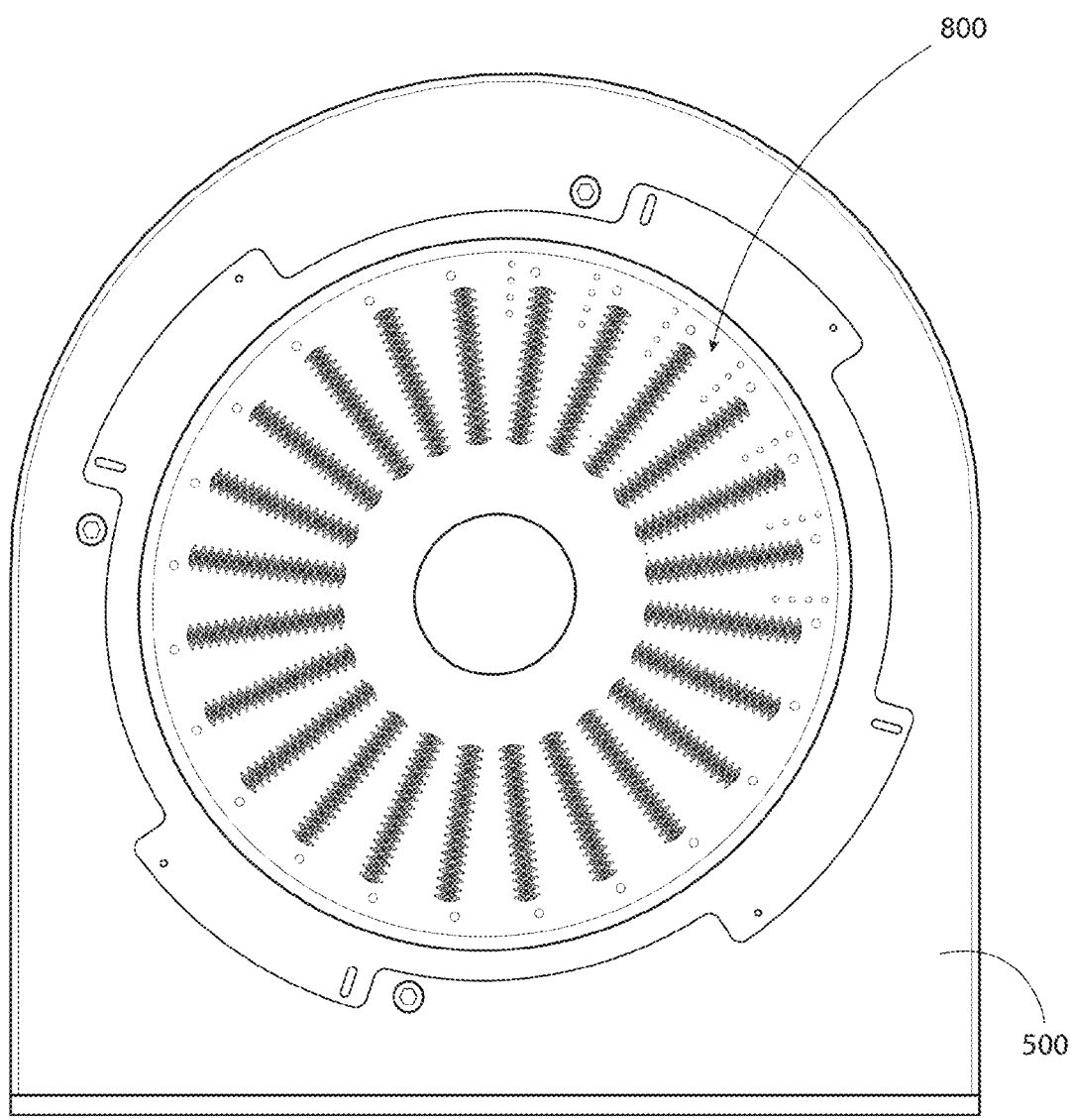
FIG. 8 illustrates an embodiment of the illuminator, having a plurality of the LED circuit boards of FIG. 7 distributed around an interior of the diffuser component.
Figure 9:
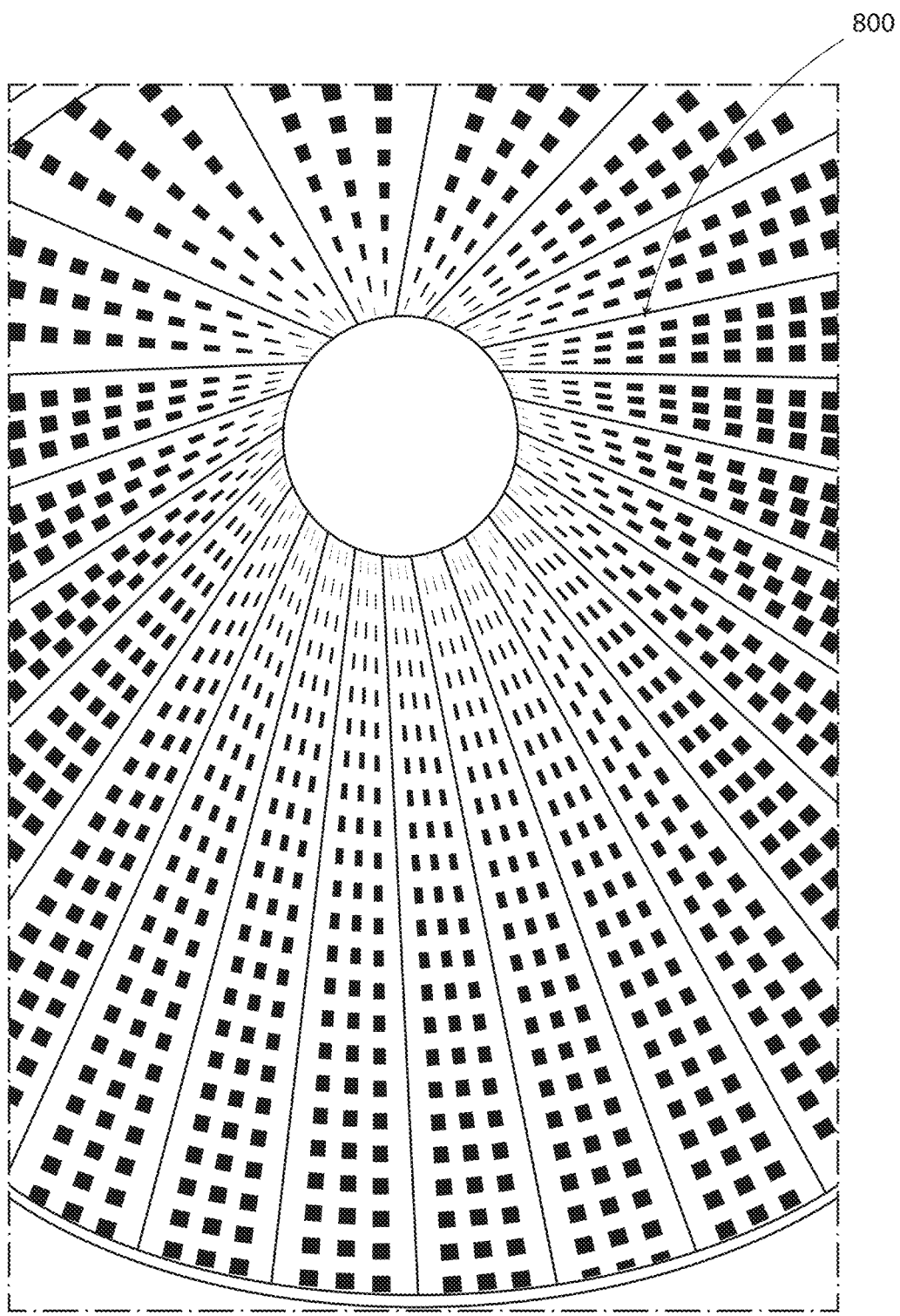
FIG. 9 shows another view of the illuminator with the plurality of LED circuit boards of FIG. 8.

As shown in FIG. 8, the illuminator 110 includes a plurality 800 of LED circuit boards 700 distributed around a surface of the diffuser component 111 (see, e.g., FIG. 5), in accordance with an embodiment. Furthermore, in accordance with an embodiment, the LED's of the LED circuit boards 700 are segregated into channels of LEDs (e.g., a red channel, a green channel, and a blue channel) which are independently controlled by the controller component 130. For example, the controller component 130 may be configured to independently change the intensity of the channels. FIG. 9 shows another view of the illuminator 110 with the plurality 800 of LED circuit boards 700. Each LED may shine onto the diffuser component 111 to illuminate a region of the diffuser component 111 immediately in the vicinity of that LED.

Figure 10:
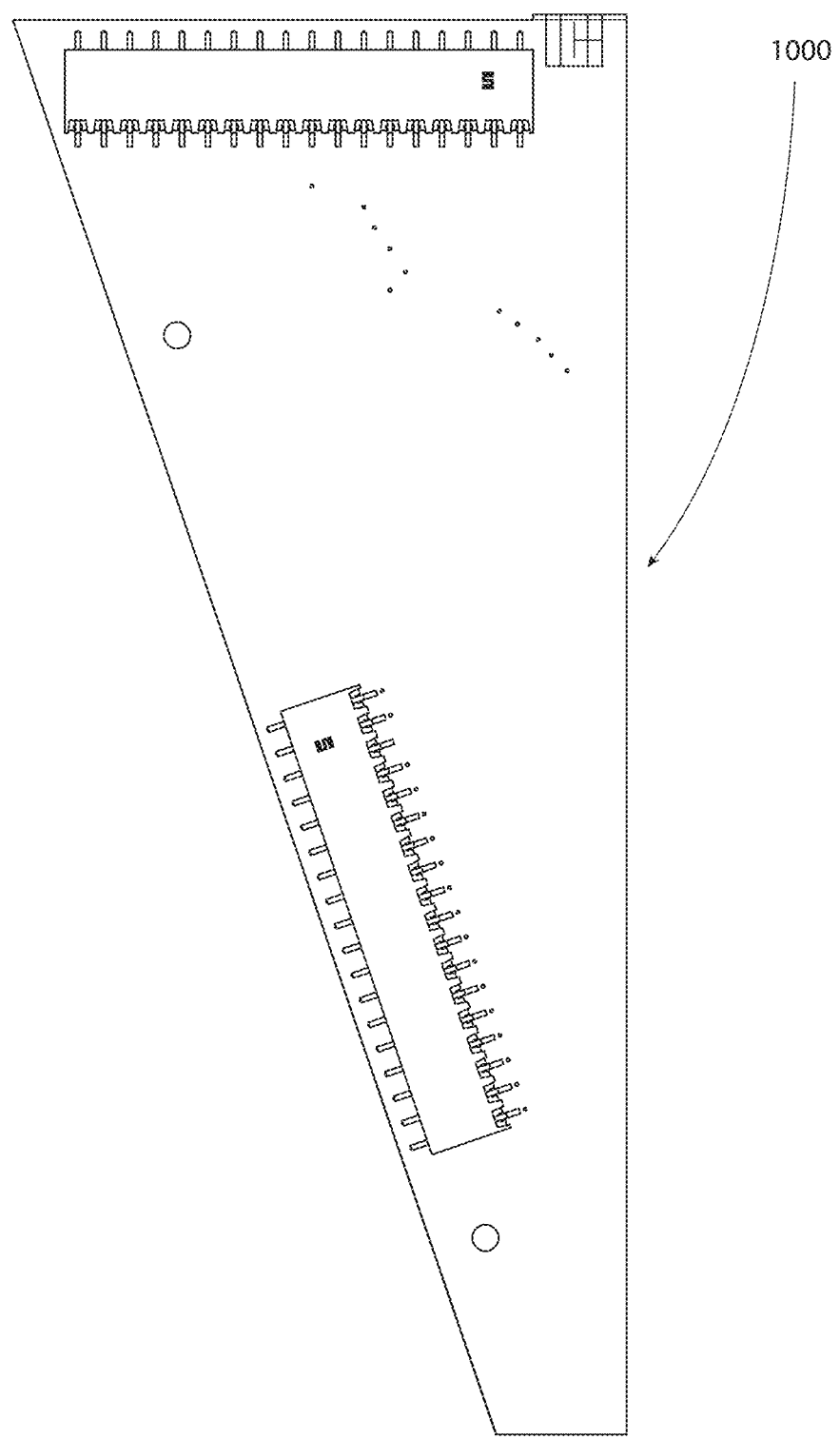
FIG. 10 illustrates an example embodiment of a power delivery circuit board of the illuminator.
Figure 11:
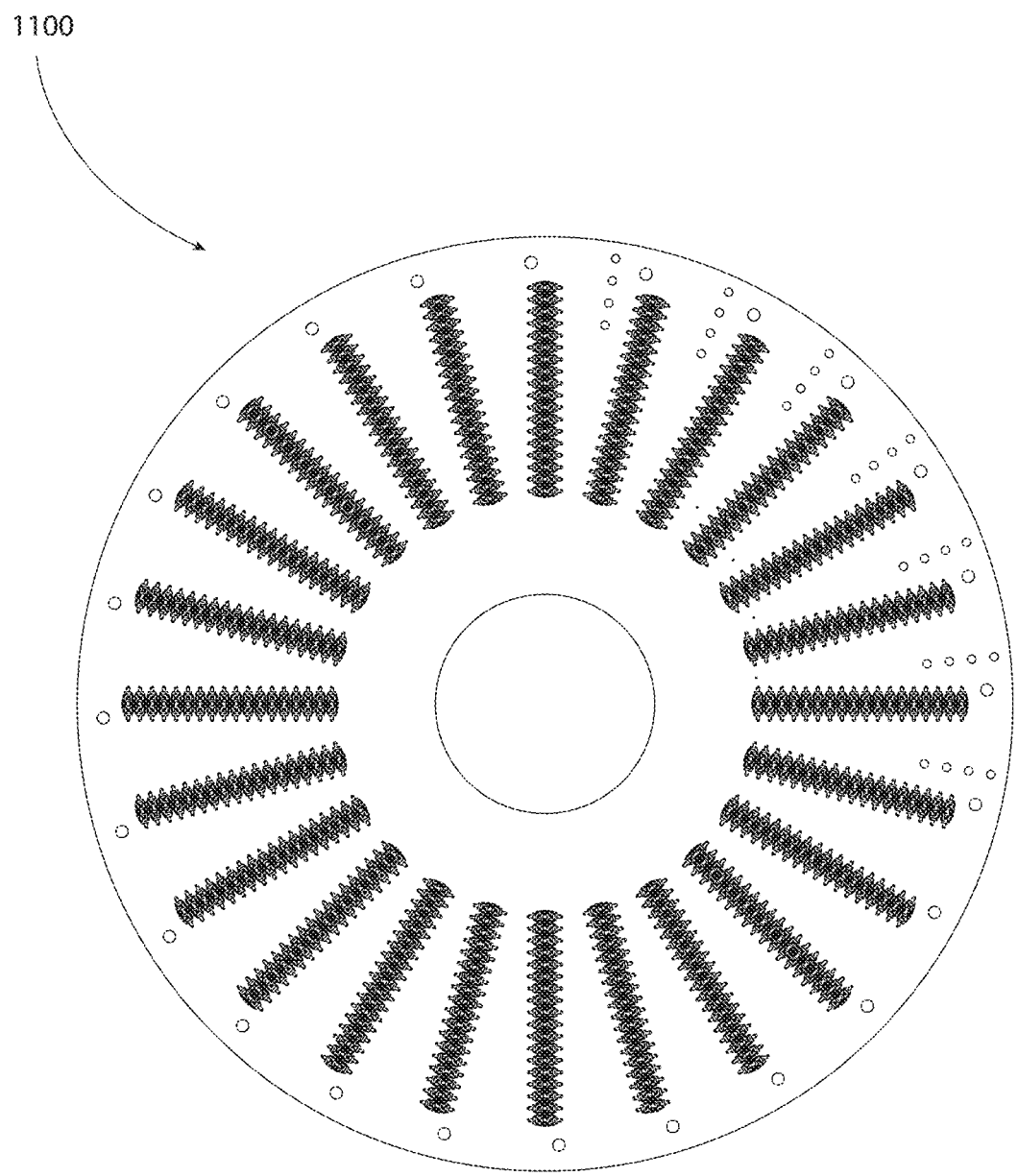
FIG. 11 illustrates an example embodiment of a power distribution circuit board of the illuminator.

FIG. 10 illustrates an example embodiment of a power delivery circuit board 1000 of the illuminator 110. The illuminator 110 includes a plurality of power delivery circuit boards 1000, one power delivery circuit board 1000 corresponding to and interfacing with one LED circuit board 700. The power delivery circuit board 1000 is substantially triangular in shape, in accordance with an embodiment. FIG. 11 illustrates an example embodiment of a power distribution circuit board 1100 of the illuminator 110. The power distribution circuit board 1100 is substantially circular in shape and is configured to operatively connect to the plurality of power delivery circuit boards 1000.

In accordance with an embodiment, the illuminator includes a power supply component 135 that is integrated with the controller component 130 (see, e.g., FIG. 1). The power distribution circuit board 1100 receives electrical power from the power supply component 135 via the controller component 130 and distributes electrical power to each of the power delivery circuit boards 1000. Each of the power delivery circuit boards 1000 delivers electrical power to a corresponding LED circuit board 700. The power supply component 135 also provides electrical power to the color camera 120, the processing component, 140, and the controller component 130.

Figure 12:
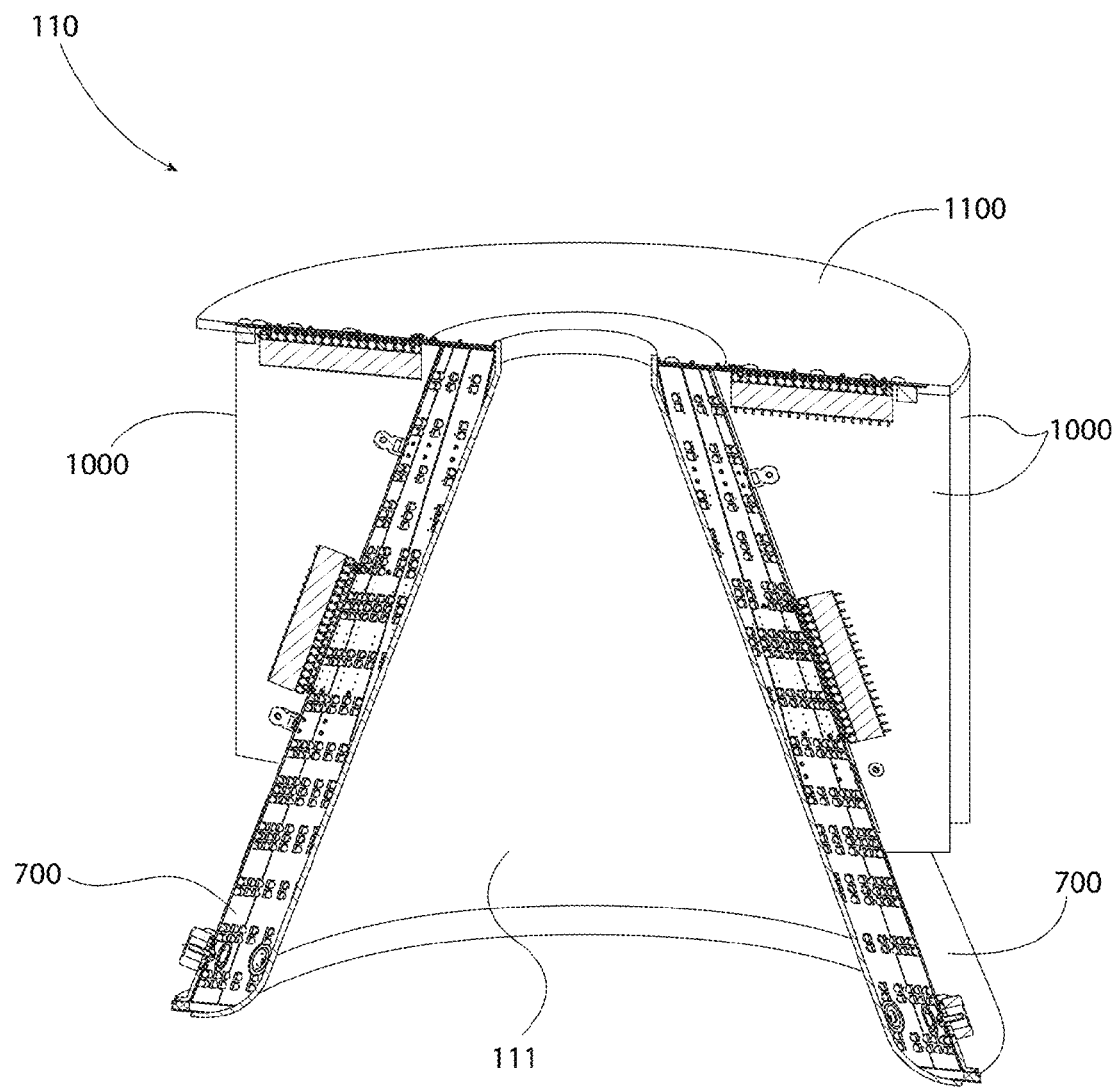
FIG. 12 illustrates a cross section of an embodiment of the illuminator showing the power distribution circuit board, the power delivery circuit boards, the LED circuit boards, and the diffuser component.
Figure 13:
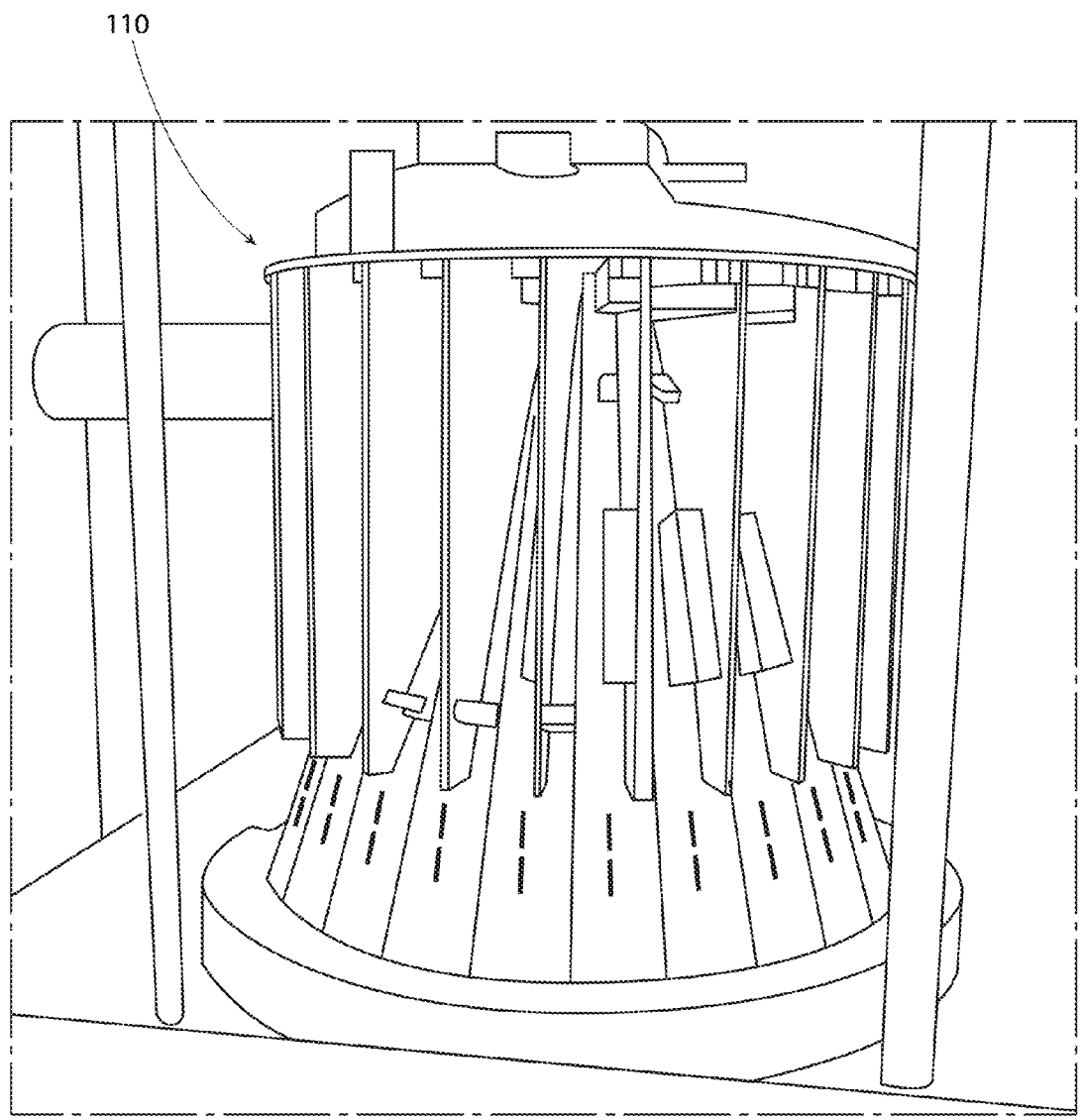
FIG. 13 illustrates an embodiment of a fully assembled illuminator.
Figure 14:
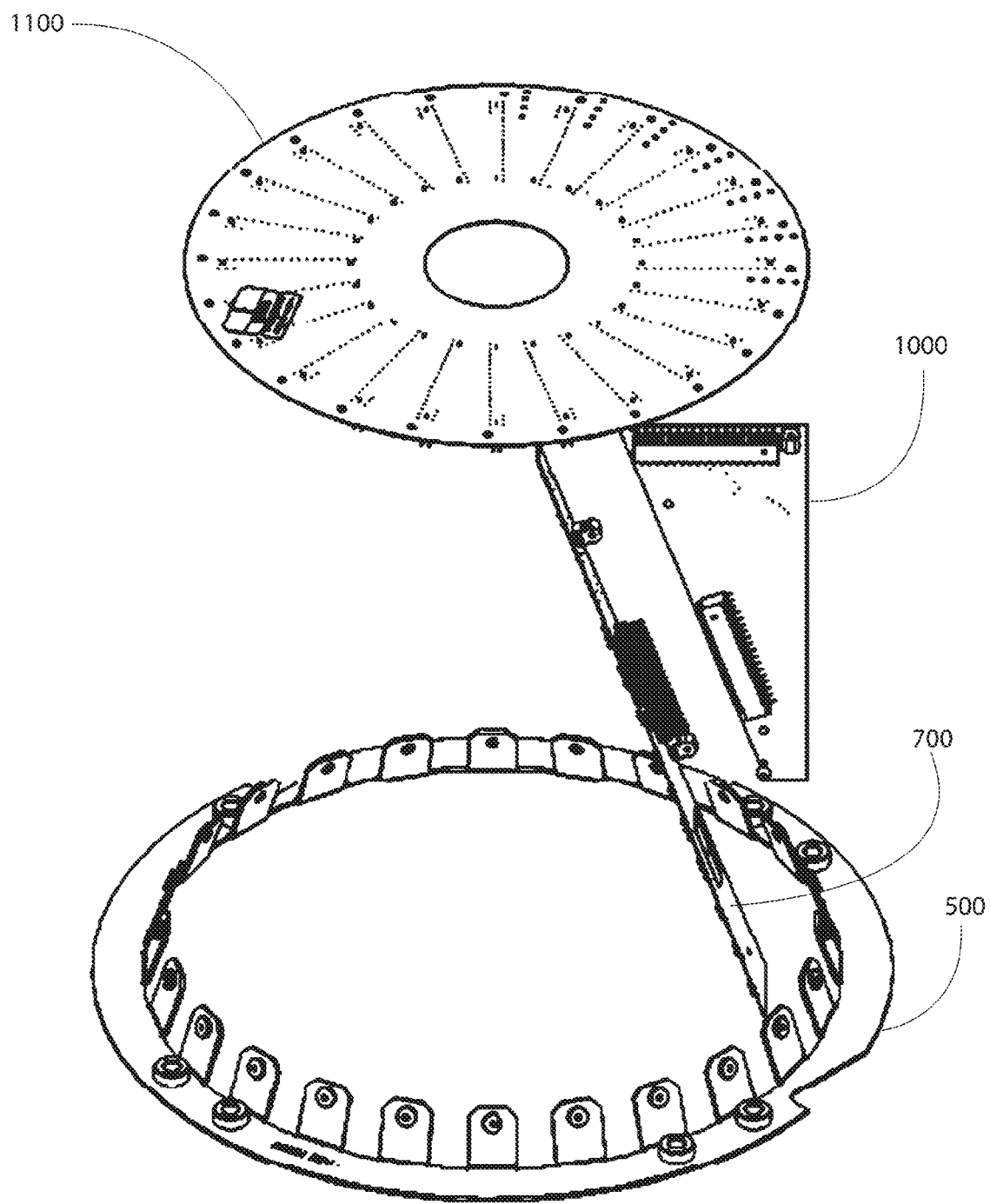
FIG. 14 illustrates a partially exploded view of a portion of an embodiment of the illuminator showing the power distribution circuit board, a power delivery circuit board, and a LED circuit board in relation to a portion of the frame component.
Figure 15:
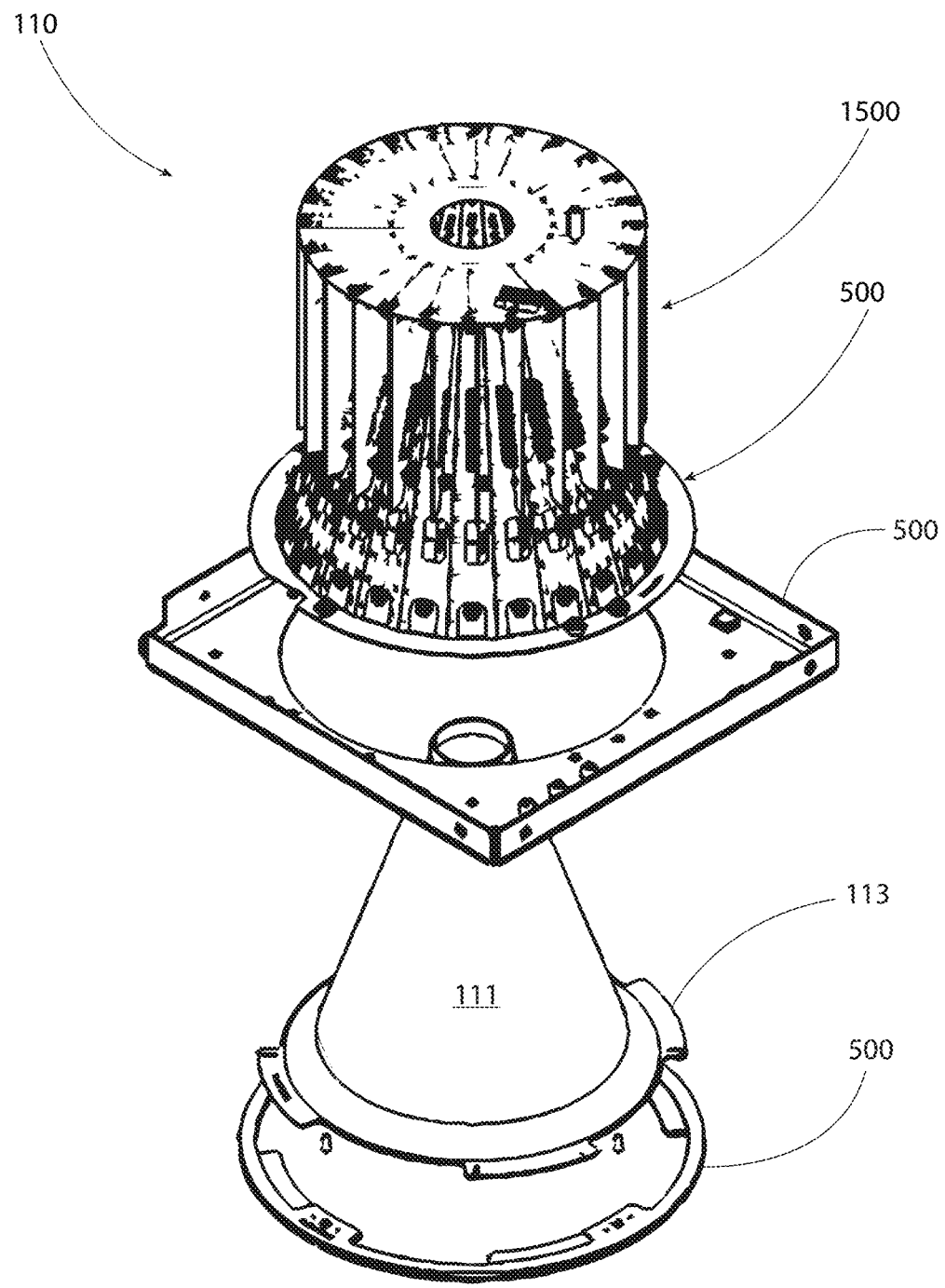
FIG. 15 illustrates a partially exploded view of the illuminator showing the diffuser component, various portions of the frame component, and the circuit boards in a fully assembled configuration.

FIG. 12 illustrates a cross section of an embodiment of the illuminator 110 showing the power distribution circuit board 1100, the power delivery circuit boards 1000, the LED circuit boards 700, and the diffuser component 111. The shapes (trapezoidal, triangular, circular) of the various circuit boards (700, 1000, 1100) facilitate the ease of assembly and maintenance of the illuminator 110. For example, if a LED on an LED circuit board fails, only that LED circuit board may be replaced, not the entire illuminator. FIG. 13 illustrates an embodiment of a fully assembled illuminator 110. FIG. 14 illustrates a partially exploded view of a portion of an embodiment of the illuminator 110 showing the power distribution circuit board 1100, a power delivery circuit board 1000, and a LED circuit board 700 in relation to a portion of the frame component 500. FIG. 15 illustrates a partially exploded view of the illuminator 110 showing the diffuser component 111, various portions of the frame component 500, and the circuit boards (700, 1000, 1100) in a fully assembled configuration 1500.

Figure 16:
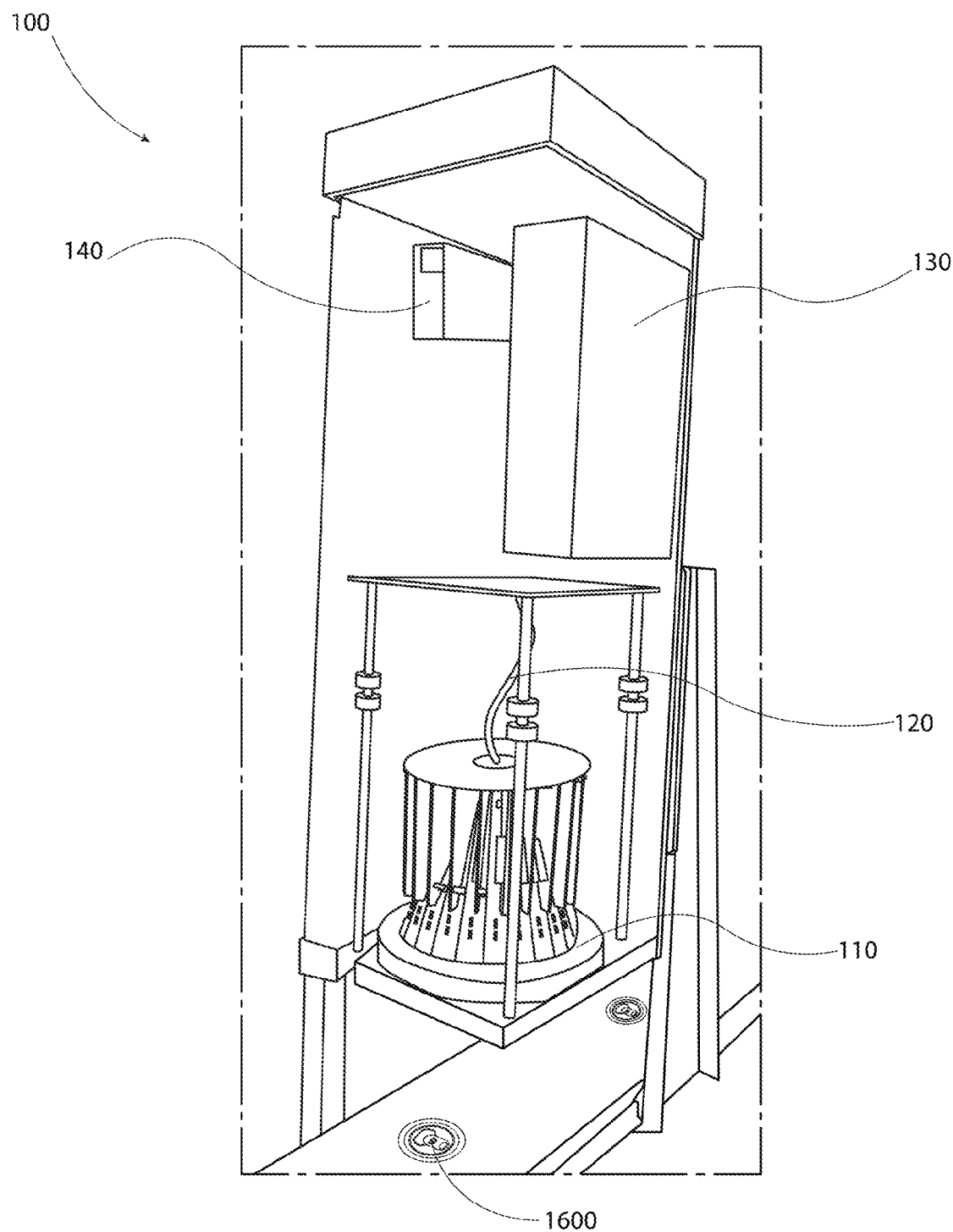
FIG. 16 illustrates an embodiment of the imaging system showing the illuminator, the camera, the controller component, and the processing component in mounted relation to each other.
Figure 17:
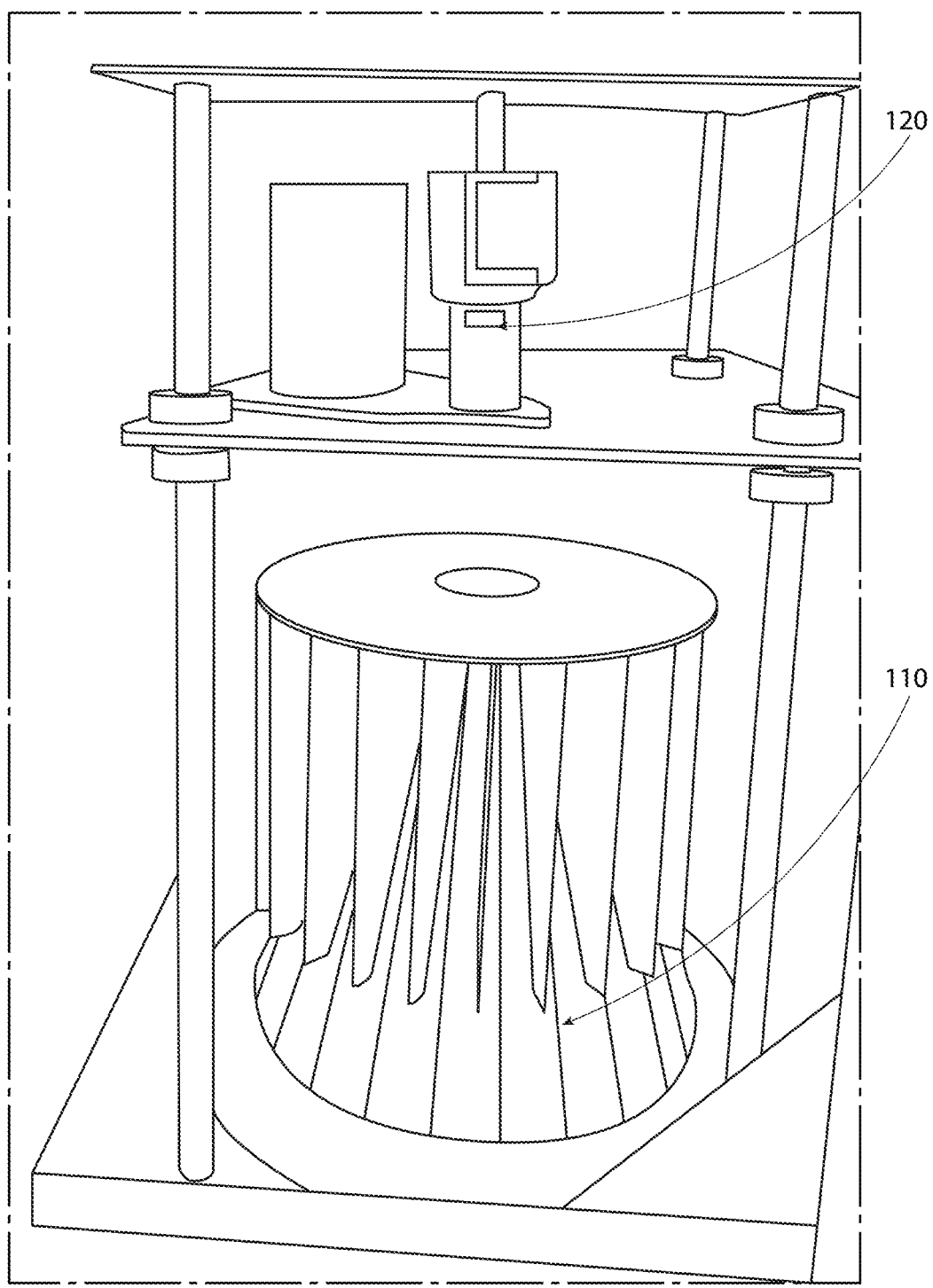
FIG. 17 illustrates a portion of the imaging system of FIG. 16 showing the camera in relation to the illuminator.

FIG. 16 illustrates an embodiment of the imaging system 100 showing the illuminator 110, the camera 120, the controller component 130, and the processing component 140 in mounted relation to each other. Also shown in FIG. 16 is a part to be inspected 1600 positioned beneath the illuminator 110. The bottom of the illuminator may be positioned as close as possible to the part to be inspected to illuminate highly curved portions of the part to be inspected. FIG. 17 illustrates a portion of the imaging system 100 of FIG. 16 showing the camera 120 in relation to the illuminator 110. The camera 120 is aligned such that the optical axis of the camera points through the center of the illuminator 110 so as to be able to image the part to be inspected 1600 which is being illuminated with the color gradient provided by the illuminator 110.

Figure 18:
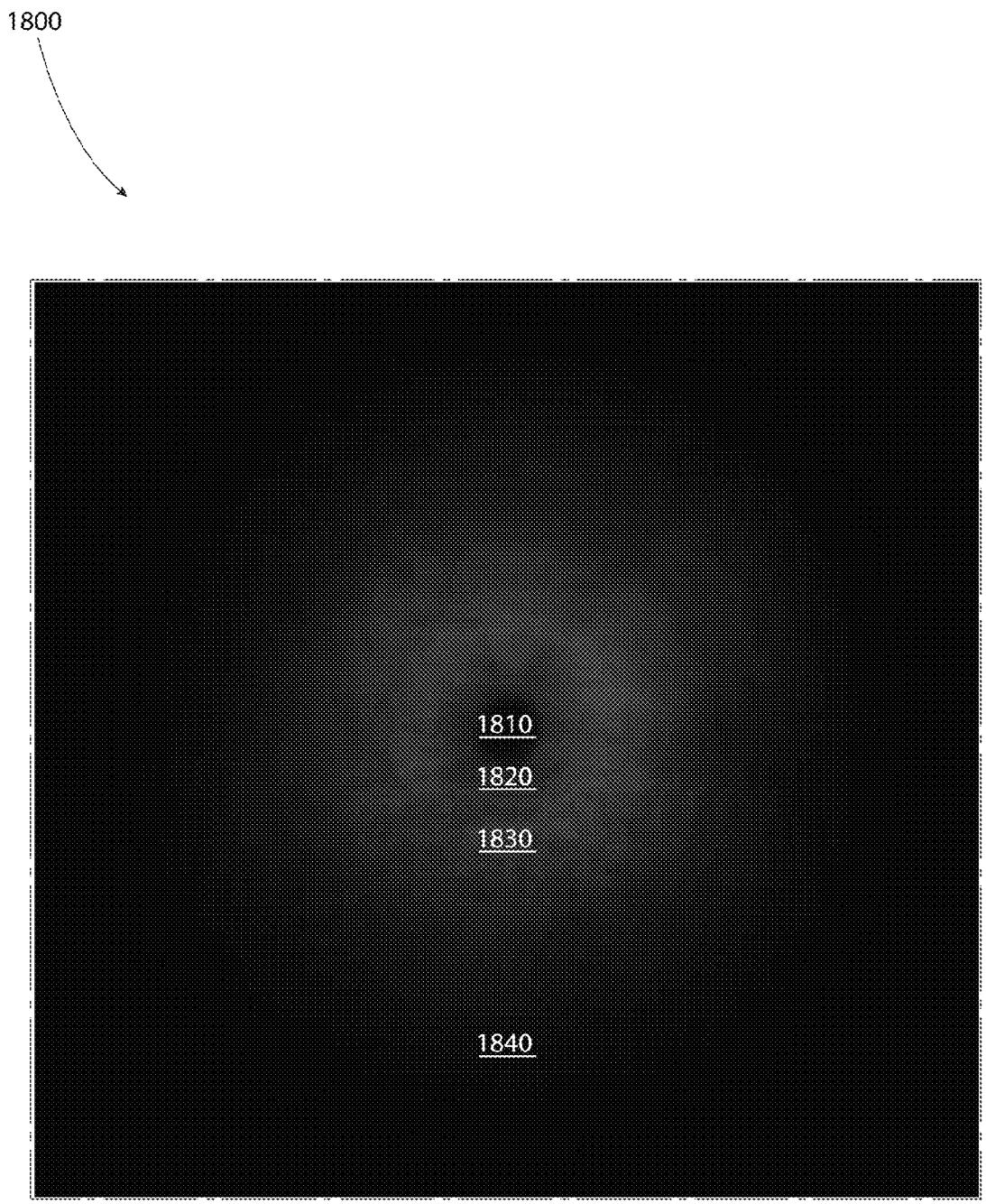
FIG. 18 illustrates the effect of the color gradient provided by the illuminator on a spherical object.

FIG. 18 illustrates the effect of the color gradient provided by the illuminator 110 on a spherical object. A color image 1800 of a shiny ball bearing is represented in FIG. 18. The color image 1800 of the ball bearing is representative of an image acquired by the system 100 of FIG. 1 having an illuminator 110 providing a gradient of three colors. The gradient of three colors transition from blue to green to red, going from a distal end of the illuminator to a proximal end of the illuminator.

At the center of the image 1800 is a black region 1810 corresponding to the reflection of the hole at the top of the illuminator 110 where the camera 120 is located. The region 1810 appears black since there is no illumination coming from that part of the illuminator 110 (i.e., no on-axis illumination), in accordance with an embodiment. The red 1820, green 1830, and blue 1840 concentric rings in the image 1800 are reflections from, respectively, the top, the center, and the bottom regions of the illuminator 110. The black 1810 and red 1820 regions correspond to places where the surface of the ball bearing is nearly horizontal. The blue 1840 region corresponds to places where the surface of the ball bearing is steeply inclined. The green 1830 region corresponds to surface inclinations of the ball bearing in between the two extremes of nearly horizontal and steeply inclined. In this manner, the color image 1800 reveals three-dimensional topographic information about the surface of the object (i.e., ball bearing) being inspected.

In accordance with an embodiment, referring at least to FIG. 12, an array of 24 trapezoid-shaped LED circuit boards 700 surrounds the diffuser component 111 of the illuminator 110, shining light onto the outside surface of the diffuser component 111. A donut-shaped power distribution circuit board 1100 is located at the top of the diffuser component 111, perpendicular to the diffuser component axis. Each LED circuit board 700 plugs into a corresponding triangle-shaped power delivery circuit board 1000, and all 24 power-delivery circuit boards 1000 plug into the single power distribution circuit board 1100. Mechanical support bracketry is located at the top and bottom of the diffuser component 111 to secure all the circuit boards.

In accordance with an embodiment, the LEDs are segregated into 8 channels (or groups), indexed 0, 1, 2 . . . 7, and the intensity of each channel can be controlled separately—typically by adjusting strobe duration. The channel intensities may be user-controlled through a software interface. Channel 0 provides a red "on-axis" illumination which sits between the camera and the top of the diffuser component. Channel 1 is also red, located at the top of the diffuser component. Channel 2 is green, located just below channel 1. Channels 3, 4, 5 and 6 are blue, located just below channel 2 and extending to the bottom of the diffuser component. Channel 7 is white, and is distributed over the entire height of the diffuser component (but not included in the "on-axis" illumination). The white channel is not ordinarily used. It was included to permit single-channel imaging in cases where the color distribution feature of the illuminator is not required.

The four (4) blue channels are included to permit fine spatial control over low-angle (or "dark field") illumination. When imaging the curl of a beverage shell or converted end, for example, low-angle illumination is typically used in order to highlight certain critical defects, such as curl dents. Small changes in illumination angle can strongly affect defect detection. The four (4) blue channels allow the user to optimize inspection performance, without having to raise or lower the illuminator, and are more critical for the detection of more vertically oriented angles of the inspected part. For example, a rapid color transition from red to blue on an inspected part may indicate a rapid curvature of the inspected part.

On-axis illumination is well known in the machine vision industry, and can take different forms. For example, a beam-splitter approach may be used where the camera and lens are moved upward to make room for a beam-splitter which allows injection of light (e.g., red light) from the side and re-directs the injected light along the optical axis through the illuminator. Alternatively, no on-axis illumination may be provided at all, allowing the camera and lens to be positioned close to the top of the illuminator. (The ball bearing image presented in FIG. 18 represents a no on-axis illumination situation—hence the dark spot in the middle of the image.)

A raw color image produced by the illuminator 110 is not typically used for inspection as-is. Instead, several different monochrome images are generated from the color image, such that each monochrome image is optimized to reveal a certain type of defect. The easiest way to think about this is to imagine the red, green and blue channels of the color image being extracted from the raw color image and treated as 3 separate monochrome images. The "red" monochrome image highlights features of the inspected object which are substantially horizontal, while the "blue" monochrome image highlights features which are strongly inclined.

An unlimited number of different color-to-monochrome transformations can be implemented. One approach is to create each monochrome pixel "m" as a linear combination of the color components "r", "g", and "b". For example, m=R*r+G*g+B*b, where R, G, and B are constants selected (through trial and error) to highlight some particular type of defect.

More generally, "m" can be represented as m=f(r,g,b), where f may be any transformation function. For example, the non-linear function $$m=(127*g+255*b)/(r+g+b) \text{ if } r+g+b>0;$$

$$m=0 \text{ otherwise,}$$

yields an image which is dark (m approaching 0) for horizontal surfaces and light (m approaching 255) for highly-inclined surfaces. In particular, the function provides sensitive and stable detection of "scrap-in-die" (dent) defects in the nominally horizontal surfaces of converted ends. In accordance with an embodiment, an illumination configuration (e.g., which channels of LEDs are turned on) may be matched with a transformation function to optimize topographic mapping of a part to be inspected for the detection of particular types of defects. Such matching may be very flexible within the system 100 and may be under software control, for example.

Figure 19:
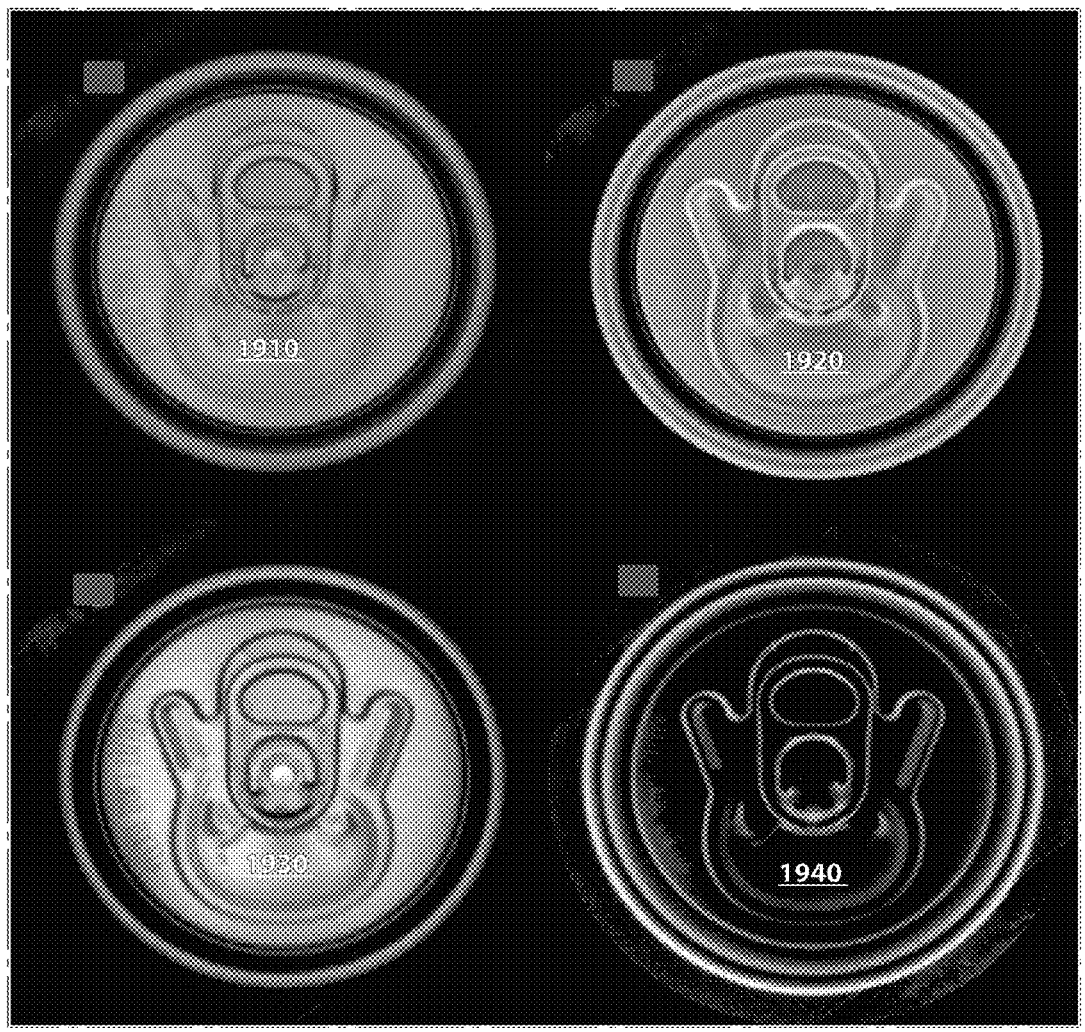
FIG. 19 illustrates an example embodiment of three monochrome images extracted or derived from a single acquired color image using the imaging system of FIG. 1.

In accordance with an embodiment, the system 100 provides a number of different views or illumination geometries of an object to be inspected from a single image acquisition. FIG. 19 illustrates an example embodiment of three monochrome images (1920, 1930, 1940) extracted or derived from a single acquired color image 1910. Since the various monochrome images (1920, 1930, 1940) are all generated from a single color image 1910, the monochrome images are all perfectly spatially aligned (or "registered") with one another. This is useful because it is sometimes easier to identify and precisely locate a particular feature (such as the tab on a converted end) in one monochrome image, and then to inspect it for defects in a different monochrome image.

Since the red, green, and blue colors are acquired simultaneously in a single color image and the resultant monochrome images are perfectly aligned, it is possible to apply color-to-monochrome transformations that permit an unlimited number of distinct monochrome images to be generated, not just three. Either CCD or CMOS camera sensors may be used with electronic shuttering, eliminating sensitivity to ambient illumination.

Systems and methods for extracting topographic information from inspected objects to identify defects in the inspected objects are provided. A part to be inspected is illuminated with at least two different colors emitted from an illuminator providing a gradient of light consisting of the at least two different colors. A single color image of the illuminated part to be inspected is acquired, providing a color-coded topographic mapping of the part to be inspected due, at least in part, to the gradient of light. Topographic monochrome views of the part to be inspected may be generated from the single color image. Each view of the topographic monochrome views may enhance a different type of feature or defect present in the part to be inspected which can be analyzed and detected. In accordance with an embodiment, this is accomplished using a color camera with a color gradient illuminator along with supporting algorithms.

While the claimed subject matter of the present application has been described with reference to certain embodiments, it will be understood by those skilled in the art that various changes may be made and equivalents may be substituted without departing from the scope of the claimed subject matter. In addition, many modifications may be made to adapt a particular situation or material to the teachings of the claimed subject matter without departing from its scope. Therefore, it is intended that the claimed subject matter not be limited to the particular embodiments disclosed, but that the claimed subject matter will include all embodiments falling within the scope of the appended claims.

What is claimed is:

1. A system comprising:
an illuminator, for illuminating a part to be inspected, configured to provide a color gradient of light transitioning between at least two different colors illuminated concurrently;
a color camera positioned near a distal end of the illuminator, defining an optical axis through an interior portion of the illuminator, wherein the color gradient of light is along the direction of the optical axis;
a controller component operatively connected to the illuminator and the color camera and configured to trigger the illuminator and the color camera to acquire a single color image of the part to be inspected located near a proximal end of the illuminator; and
a processing component operatively connected to the color camera and configured to receive and process the single color image to generate two or more topographic monochrome views of the part to be inspected from the single color image based on the color gradient of light provided by the illuminator.

2. The system of claim 1, wherein the illuminator is configured to illuminate the part to be inspected such that the acquired single color image provides a color-coded topographic mapping of the part to be inspected.

3. The system of claim 1, wherein the two or more topographic monochrome views are spatially registered with each other.

4. The method of claim 1, wherein the illuminator includes a plurality of light-emitting diodes, providing the at least two different colors, that are segregated into channels where each channel is independently controllable by the controller component.

5. The system of claim 1, further comprising a power supply component configured to supply power to the illuminator, the color camera, the processing component, and the controller component.

6. The system of claim 1, wherein the controller component and the processing component are configured to provide a defined combination of illumination of the part to be inspected and a color-to-monochrome transformation of the acquired single color image of the part to be inspected to allow generation of a topographic monochrome view of the part to be inspected that enhances a defined type of defect present in the part to be inspected for detection of such defect.

7. The system of claim 1, wherein the illuminator includes a plurality of light-emitting diodes to produce a color gradient of light that progresses substantially from a red color to a green color, and from the green color to a blue color.

8. An illuminator comprising:
a power distribution circuit board;
a plurality of power delivery circuit boards each interfacing with the power distribution circuit board; and
a plurality of light-emitting diode circuit boards each interfacing with a corresponding power delivery circuit board of the plurality of power delivery circuit boards, wherein each light-emitting diode circuit board of the plurality of light-emitting diode circuit boards includes a plurality of light-emitting diodes of at least two differing colors distributed thereon to provide a color gradient of light of at least two colors generally along an axis, progressing from a proximal end of the light-emitting diode circuit board to a distal end of the light-emitting diode circuit board.

9. The illuminator of claim 8, wherein the power distribution circuit board is substantially circular in shape, each of the plurality of power delivery circuit boards is substantially triangular in shape, and each of the plurality of light-emitting-diode circuit boards is substantially trapezoidal in shape.

10. The illuminator of claim 8, wherein each of the power delivery circuit boards interfaces with the power distribution circuit board at substantially a right angle, and each of the plurality of light-emitting diode circuit boards interfaces with a corresponding power delivery circuit board of the plurality of power delivery circuit boards at substantially a right angle.

11. The illuminator of claim 8, further comprising a diffuser component configured to reside substantially within an interior portion of the illuminator to diffuse light emitted by the plurality of light-emitting diodes therethrough.

12. The illuminator of claim 11, wherein the diffuser component is substantially conical in shape.

13. The illuminator of claim 12, wherein the diffuser component includes a flared lip portion along a proximal end of the substantially conical shape.

14. The illuminator of claim 8, wherein the color gradient of light progresses substantially from a blue color to a green color, and from the green color to a red color.

15. The illuminator of claim 8, wherein each of the at least two differing colors of light-emitting diodes are distributed substantially circumferentially and symmetrically around the illuminator.

16. The illuminator of claim 8, wherein the plurality of light-emitting diode circuit boards are arranged to form a substantially conical configuration.

17. The illuminator of claim 8, further comprising a beam splitter component proximate a distal end of the illuminator providing on-axis illumination along a defined optical axis of the illuminator.

18. A method comprising:
illuminating a part to be inspected concurrently with at least two different colors emitted from an illuminator that generates a color gradient of light of the at least two different colors, wherein the color gradient of light is along a direction of an optical axis through the illuminator defined by a color camera and associated lens positioned proximate a distal end of the illuminator, and wherein the part to be inspected is positioned proximate a proximal end of the illuminator;
acquiring a single color image of the illuminated part to be inspected with the color camera and associated lens, wherein the single color image provides a color-coded topographic mapping of the part to be inspected due, at least in part, to the color gradient of light; and
generating two or more topographic monochrome views of the part to be inspected from the single color image.

19. The method of claim 18, wherein each view of the two or more topographic monochrome views enhances a different type of defect present in the part to be inspected.

20. The method of claim 18, further comprising detecting at least one defect of the part to be inspected present in at least one of the two or more topographic monochrome views.

* * * * *